(12) United States Patent
Kim et al.

(10) Patent No.: US 9,822,200 B2
(45) Date of Patent: *Nov. 21, 2017

(54) LIGAND COMPOUND, TRANSITION METAL COMPOUND, AND CATALYSTIC COMPOSITION INCLUDING THE SAME

(71) Applicant: LG CHEM, LTD., Seoul (KR)

(72) Inventors: Dong Eun Kim, Daejeon (KR); A Rim Kim, Daejeon (KR); Jin Sam Gong, Daejeon (KR); Seung Hwan Jung, Daejeon (KR); Hae Woong Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/110,596

(22) PCT Filed: Nov. 6, 2015

(86) PCT No.: PCT/KR2015/011892
§ 371 (c)(1),
(2) Date: Jul. 8, 2016

(87) PCT Pub. No.: WO2016/072783
PCT Pub. Date: May 12, 2016

(65) Prior Publication Data
US 2016/0326281 A1    Nov. 10, 2016

(30) Foreign Application Priority Data
Nov. 7, 2014    (KR) .................. 10-2014-0154389

(51) Int. Cl.
*C08F 10/00* (2006.01)
*C08F 4/02* (2006.01)
*C08F 4/6592* (2006.01)
*C08F 110/02* (2006.01)
*C08F 210/16* (2006.01)
*C07F 7/10* (2006.01)
*C07F 7/28* (2006.01)
*C07F 17/00* (2006.01)

(52) U.S. Cl.
CPC .............. *C08F 210/16* (2013.01); *C07F 7/10* (2013.01); *C07F 7/28* (2013.01); *C07F 17/00* (2013.01); *C08F 4/6592* (2013.01)

(58) Field of Classification Search
None
See application file for complete search history.

(56) References Cited

U.S. PATENT DOCUMENTS

| 5,064,802 A | 11/1991 | Stevens et al. |
| 6,015,916 A | 1/2000 | Sullivan et al. |
| 6,548,686 B2 | 4/2003 | Nabika et al. |
| 2002/0147286 A1 | 10/2002 | Resconi et al. |
| 2004/0236115 A1 | 11/2004 | Nifantev et al. |
| 2005/0010039 A1 | 1/2005 | Graf et al. |
| 2007/0135623 A1 | 6/2007 | Voskoboynikov et al. |
| 2008/0287692 A1 | 11/2008 | Nifant'ev et al. |
| 2011/0288249 A1 | 11/2011 | Voskoboynikov et al. |
| 2012/0202956 A1 | 8/2012 | Voskoboynikov et al. |
| 2013/0203949 A1 | 8/2013 | Lee et al. |
| 2015/0011770 A1 | 1/2015 | Lee et al. |
| 2015/0025204 A1 | 1/2015 | Lee et al. |
| 2015/0361196 A1 | 12/2015 | Do et al. |

FOREIGN PATENT DOCUMENTS

| EP | 2 559 695 A2 | 2/2013 |
| EP | 2 980 104 A1 | 2/2016 |
| JP | 2004-530689 A | 10/2004 |
| KR | 2001-0112350 A | 12/2001 |
| KR | 10-1271904 B1 | 6/2013 |
| KR | 10-2013-0116395 A | 10/2013 |
| WO | WO 03/078480 A2 | 9/2003 |

OTHER PUBLICATIONS

Chen et al., "A Novel Phenolate "Constrained Geometry" Catalyst System. Efficient Synthesis, Structural Characterization, and α-Olefin Polymerization Catalysis", Organometallics, vol. 16, No. 26, 1997, pp. 5958-5963.
Christie et al., "Novel Routes to Bidentate Cyclopentadienyl-Alkoxide Complexes of Titanium: Synthesis of ($\eta^5$-σ-$C_5R^1_4CHR^2CH_2CR^3R^4O$)$TiCl_2$", Organometallics, vol. 18, No. 3, 1999, pp. 348-359.
Gibson et al., "Advances in Non-Metallocene Olefin Polymerization Catalysis", Chemical Reviews, vol. 103, No. 1, 2003, pp. 283-315.
Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group", Organometallics, vol. 17, No. 9, 1998, pp. 1652-1654.
International Search Report (PCT/ISA/210) issued in PCT/KR2015/011892, dated Jan. 14, 2016.
Rau et al., "Synthesis and application in high-pressure polymerization of a titanium complex with a linked cyclopentadienyl-phenoxide ligand", Journal of Organometallic Chemistry, vol. 608, 2000, pp. 71-75.
Ryabov et al., "Constrained geometry complexes of titanium (IV) and zirconium (IV) involving cyclopentadienyl fused to thiophene ring", Journal of Organometallic Chemistry, vol. 690, 2005, pp. 4213-4221.
Ryabov et al., "Zirconium Complexes with Cyclopentadienyl Ligands Involving Fused a Thiophene Fragment", Organometallics, vol. 21, No. 14, 2002, pp. 2842-2855.

(Continued)

*Primary Examiner* — Yun Qian
(74) *Attorney, Agent, or Firm* — Birch, Stewart, Kolasch & Birch, LLP

(57) ABSTRACT

The present invention relates to a novel ligand compound, a transition metal compound, and a catalytic composition including the same. The novel ligand compound and the transition metal compound of the present invention are useful as a polymerization reaction catalyst in preparing an olefin-based polymer having low density. In addition, an olefin polymer polymerized using a catalytic composition including the transition metal compound is capable of being prepared to a high molecular weight product having a low melt index (MI).

7 Claims, No Drawings

(56) References Cited

OTHER PUBLICATIONS

Turner et al., "Facile resolution of constrained geometry indenyl-phenoxide ligation", Chemical Communications, 2003, pp. 1034-1035.
Zhang et al., "Constrained Geometry Tetramethylcyclopentadienyl-phenoxytitanium Dichlorides: Template Synthesis, Structures, and Catalytic Properties for Ethylene Polymerization", Organometallics, vol. 23, No. 3, 2004, pp. 540-546.
Extended European Search Report dated Sep. 19, 2017 in EP Application No. 15857360.0.

LIGAND COMPOUND, TRANSITION METAL COMPOUND, AND CATALYSTIC COMPOSITION INCLUDING THE SAME

FIELD OF THE INVENTION

This application claims priority to and the benefits of Korean Patent Application No. 10-2014-0154389, filed with the Korean Intellectual Property Office on Nov. 7, 2014, the entire contents of which are incorporated herein by reference.

The present specification relates to a ligand compound having a novel structure, a transition metal compound and a catalytic composition including the same.

DESCRIPTION OF THE RELATED ART

Dow Chemical Company introduced [$Me_2Si(Me_4C_5)$ NtBu]$TiCl_2$ (Constrained-Geometry Catalyst, abbreviated as CGC hereinafter) in early 1990s (U.S. Pat. No. 5,064,802), and advantages of the CGC in a copolymerization reaction of ethylene and alpha-olefin compared to metallocene catalysts that have been known in the art may be summarized into two points as follows: (1) CGC produces a high molecular weight polymer while exhibiting high activity even at high polymerization temperatures, and (2) copolymerizability of alpha-olefin having large steric hindrance such as 1-hexene and 1-octent is also very outstanding. Besides, as other properties of CGC in a polymerization reaction have been gradually known, efforts to synthesize derivatives of CGC to use as a polymerization catalyst have been active both in academics and industries.

As one of the approaches, synthesis of metal compounds, in which other various bridges instead of a silicon bridge and a nitrogen substituent are introduced, and polymerization thereof have been tried. Representative metal compounds that have been known until recently may be listed as the following compounds (1) to (4) (Chem. Rev. 2003, 103, 283).

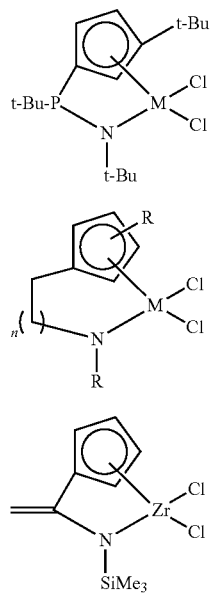

In the compounds (1) to (4), phosphorous (1), ethylene or propylene (2), methylidene (3), and methylene (4) bridges are introduced, respectively, instead of a silicon bridge having a CGC structure, however, improved results in terms of activity or copolymerization performance were not able to be obtained compared to CGC when the compounds (1) to (4) were used in ethylene polymerization or copolymerization with alpha-olefin.

In addition, as another approach, compounds having an oxido ligand instead of an amido ligand of the CGC have been actively synthesized, and polymerization using the same has been tried in some cases. Examples thereof are summarized as follows.

Compound (5) has been reported by T. J. Marks et al. and has a cyclopentadiene (Cp) derivative and an oxido ligand being cross-linked by an ortho-phenylene group (Organometallics 1997, 16, 5958). Compounds having the same cross-link and polymerization using the same have been also reported by Mu et al. (Organometallics 2004, 23, 540). In addition, an indenyl ligand and an oxido ligand being cross-linked by an ortho-phenylene group have been reported by Rothwell et al. (Chem. Commun. 2003, 1034). Compound (6) has been reported by Whitby et al., and has a cyclopentanienyl ligand and an oxido ligand being bridged by 3 carbons (Organometallics 1999, 18, 348), and such catalysts have been reported to exhibit activity in syndiotactic polystyrene polymerization. Similar compounds also have been reported by Hessen et al. (Organometallics 1998, 17, 1652). Compound (7) has been reported by Rau et al., and exhibits activity in ethylene polymerization and ethylene/1-hexene copolymerization at a high temperature and a high pressure (210° C., 150 mPa) (J. Organomet. Chem. 2000, 608, 71). After that, Sumitomo Corporation applied for a patent on the synthesis of catalysts having similar structures thereto (8) and high temperature and high pressure polymerization using the same (U.S. Pat. No. 6,548,686). However, among the above-mentioned attempts, only small numbers of catalysts are actually used in commercial factories. Accordingly, catalysts having enhanced polymerization efficiency, and methods for simply preparing such catalysts have been required.

PRIOR ART DOCUMENTS

U.S. Pat. No. 5,064,802
U.S. Pat. No. 6,548,686

NON-PATENT DOCUMENTS

Chem. Rev. 2003, 103, 283
Organometallics 1997, 16, 5958
Organometallics 2004, 23, 540
Chem. Commun. 2003, 1034
Organometallics 1999, 18, 348
Organometallics 1998, 17, 1652
J. Organomet. Chem. 2000, 608, 71

DISCLOSURE OF THE INVENTION

Technical Problem

An object of the present invention is to provide a novel transition metal compound.

Another object of the present invention is to provide a novel ligand compound.

Still another object of the present invention is to provide a catalytic composition including the transition metal compound.

Technical Solution

One embodiment of the present specification provides a transition metal compound represented by the following Chemical Formula 1:

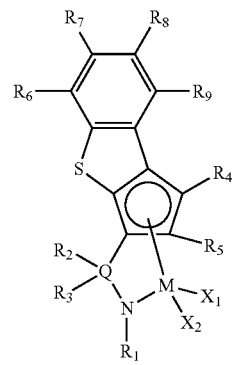

[Chemical Formula 1]

In Chemical Formula 1,
$R_1$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_2$ and $R_3$ are each independently hydrogen; halogen alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkylamido having 1 to 20 carbon atoms; arylamido having 6 to 20 carbon atoms; or alkylidene having 1 to 20 carbon atoms, $R_4$ to $R_9$ are each independently a metalloid radical of a group 14 metal substituted with hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or hydrocarbyl having 1 to 20 carbon atoms, two or more of $R_2$ to $R_9$ adjacent to each other may be linked to each other to form a ring, Q is Si, C, N, P or S, M is a group 4 transition metal, and $X_1$ and $X_2$ are each independently hydrogen, halogen, alkyl having 1 to 20 carbon atoms, alkenyl having 2 to 20 carbon atoms, aryl having 6 to 20 carbon atoms, alkylaryl having 7 to 20 carbon atoms, arylalkyl having 7 to 20 carbon atoms, alkylamino having 1 to 20 carbon atoms, arylamino having 6 to 20 carbon atoms or alkylidene having 1 to 20 carbon atoms.

Another embodiment of the present specification provides a ligand compound represented by the following Chemical Formula 2:

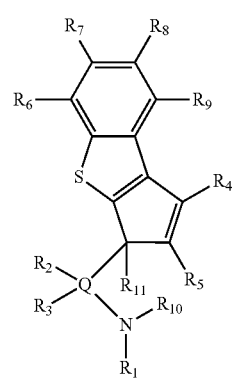

[Chemical Formula 2]

In Chemical Formula 2, $R_1$, $R_{10}$ and $R_{11}$ are hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_2$ and $R_3$ are each independently hydrogen; halogen alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; alkylamido having 1 to 20 carbon atoms; arylamido having 6 to 20 carbon atoms; or alkylidene having 1 to 20 carbon atoms, $R_4$ to $R_9$ are each independently a metalloid radical of a group 14 metal substituted with hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or hydrocarbyl having 1 to 20 carbon atoms, two or more of $R_2$ to $R_9$ adjacent to each other may be linked to each other to form a ring, and Q is Si, C, N, P or S.

Still another embodiment of the present specification provides a catalytic composition including the transition metal compound of Chemical Formula 1.

Advantageous Effects

A novel ligand compound and a transition metal compound of the present invention can be useful as a polymerization reaction catalyst in preparing an olefin-based polymer of a low density area having a high molecular weight, and a high molecular weight polymer having a low melt index (MI) can be obtained.

MODE FOR CARRYING OUT THE INVENTION

Hereinafter, the present invention will be described in more detail in order to illuminate the present invention.

Terms or words used in the present specification and the claims are not to be interpreted limitedly to common or dictionary definitions, and shall be interpreted as meanings and concepts corresponding to technological ideas of the present invention based on a principle in which the inventors may suitably define the concepts of terms in order to describe the invention in the best possible way.

For accomplishing one technical object of the present invention, the present invention provides a transition metal compound represented by the following Chemical Formula 1:

[Chemical Formula 1]

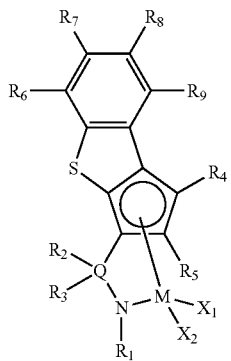

In Chemical Formula 1, $R_1$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_2$ and $R_3$ are each independently hydrogen; halogen alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkylamido having 1 to 20 carbon atoms; arylamido having 6 to 20 carbon atoms; or alkylidene having 1 to 20 carbon atoms, $R_4$ to $R_9$ are each independently a metalloid radical of a group 14 metal substituted with hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or hydrocarbyl having 1 to 20 carbon atoms, two or more of $R_2$ to $R_9$ adjacent to each other may be linked to each other to form a ring, Q is Si, C, N, P or S, M is a group 4 transition metal, and $X_1$ and $X_2$ are each independently hydrogen, halogen, alkyl having 1 to 20 carbon atoms, alkenyl having 2 to 20 carbon atoms, aryl having 6 to 20 carbon atoms, alkylaryl having 7 to 20 carbon atoms, arylalkyl having 7 to 20 carbon atoms, alkylamino having 1 to 20 carbon atoms, arylamino having 6 to 20 carbon atoms or alkylidene having 1 to 20 carbon atoms.

The transition metal compound of Chemical Formula 1 described in the present specification forms a structure in which cyclopentadiene fused with benzothiophene through a ring-type bond, and an amido group (N-Rd are stably cross-linked by Q (Si, C, N or P), and a group 4 transition metal coordinately bonds thereto.

When the catalytic composition is used in olefin polymerization, polyolefin having properties such as high activity, a high molecular weight and high copolymerizability is capable of being produced even at high polymerization temperatures. Particularly, from structural characteristics of the catalyst, linear low density polyethylene having density of approximately 0.850 g/cc to 0.930 g/cc may be prepared, and, since a large amount of alpha-olefin may be introduced, polymers (elastomers) with a very low density area of less than 0.910 g/cc may also be prepared.

In the present specification, the alkyl and the alkenyl are alkyl having 1 to 20 carbon atoms and alkenyl having 2 to 20 carbon atoms, respectively, and may be linear or branched.

In the present specification, the silyl may be silyl substituted with alkyl having 1 to 20 carbon atoms, and examples thereof may include trimethylsilyl or triethylsilyl.

In the present specification, the aryl includes monocyclic or multicyclic aryl, and specifically, includes phenyl, naphthyl, anthryl, phenanthryl, crycenyl, pyrenyl and the like.

$R_1$ to $R_9$ are each independently unsubstituted or substituted, and when substituted, examples of the substituent may include halogen, alkyl having 1 to 20 carbon atoms, hydrocarbyl having 1 to 20 carbon atoms, alkoxy having 1 to 20 carbon atoms, or aryloxy having 6 to 20 carbon atoms.

According to one embodiment of the present invention, in Chemical Formula 1, $R_1$ may be alkyl having 1 to 20 carbon atoms; alkoxy having 1 to 20 carbon atoms; aryl having 6 to 20 carbon atoms; arylalkoxy having 7 to 20 carbon atoms; arylalkyl having 7 to 20 carbon atoms; or alkylaryl having 7 to 20 carbon atoms.

According to one embodiment of the present invention, in Chemical Formula 1, $R_1$ may be alkyl having 1 to 20 carbon atoms; aryl having 6 to 20 carbon atoms; arylalkoxy having 7 to 20 carbon atoms; or arylalkyl having 7 to 20 carbon atoms.

According to one embodiment of the present invention, in Chemical Formula 1, $R_1$ may be methyl, ethyl, propyl, butyl, isobutyl, t-butyl, isopropyl, cyclohexyl, benzyl, phenyl, methoxyphenyl, ethoxyphenyl, fluorophenyl, bromophenyl, chlorophenyl, dimethylphenyl or diethylphenyl.

According to one embodiment of the present invention, in Chemical Formula 1, $R_2$ and $R_3$ may be each independently hydrogen; alkyl having 1 to 20 carbon atoms; aryl having 6 to 20 carbon atoms; or alkylaryl having 6 to 20 carbon atoms.

According to one embodiment of the present invention, in Chemical Formula 1, $R_2$ and $R_3$ may be each independently hydrogen; alkyl having 1 to 20 carbon atoms; or aryl having 6 to 20 carbon atoms.

According to one embodiment of the present invention, $R_4$ to $R_9$ may be each independently hydrogen; alkyl having 1 to 20 carbon atoms; aryl having 6 to 20 carbon atoms; alkylaryl having 7 to 20 carbon atoms; or arylalkyl having 7 to 20 carbon atoms.

According to one embodiment of the present invention, $R_4$ and $R_5$ are the same as or different from each other, and may be each independently alkyl having 1 to 20 carbon atoms; or aryl having 6 to 20 carbon atoms.

According to one embodiment of the present invention, $R_4$ and $R_5$ are the same as or different from each other, and may be each independently alkyl having 1 to 6 carbon atoms.

According to one embodiment of the present invention, $R_4$ and $R_5$ may be methyl, ethyl or propyl.

According to one embodiment of the present invention, $R_6$ to $R_9$ are the same as or different from each other, and may be each independently hydrogen; alkyl having 1 to 20 carbon atoms; aryl having 6 to 20 carbon atoms; alkylaryl having 7 to 20 carbon atoms; or arylalkyl having 7 to 20 carbon atoms.

According to one embodiment of the present invention, $R_6$ to $R_9$ are the same as or different from each other, and may be each independently hydrogen; or alkyl having 1 to 20 carbon atoms.

According to one embodiment of the present invention, $R_6$ to $R_9$ are the same as or different from each other, and may be each independently hydrogen or methyl.

According to one embodiment of the present invention, M may be Ti, Hf or Zr.

According to one embodiment of the present invention, $X_1$ and $X_2$ are the same as or different from each other, and may be each independently hydrogen, halogen, alkyl having 1 to 20 carbon atoms or alkenyl having 2 to 20 carbon atoms.

According to one embodiment of the present invention, in Chemical Formula 1, $R_1$ may be hydrogen; alkyl having 1 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_2$ and $R_3$ may be each independently hydrogen; alkyl having 1 to 20 carbon atoms; aryl having 6 to 20 carbon atoms; or alkylaryl having 6 to 20 carbon atoms, $R_4$ to $R_9$ may be each independently hydrogen; alkyl having 1 to 20 carbon atoms; aryl having 6 to 20 carbon atoms; alkylaryl having 7 to 20 carbon atoms; or arylalkyl having 7 to 20 carbon atoms, two or more of $R_2$ to $R_9$ adjacent to each other may be linked to each other to form an aliphatic ring having 5 to 20 carbon atoms or an aromatic ring having 6 to 20 carbon atoms;

the aliphatic ring or the aromatic ring may be substituted with halogen, alkyl having 1 to 20 carbon atoms, alkenyl having 2 to 20 carbon atoms, or aryl having 6 to 20 carbon atoms, and Q may be Si, C, N or P.

According to one embodiment of the present invention, in Chemical Formula 1, $R_1$ may be alkyl having 1 to 20 carbon atoms; aryl having 6 to 20 carbon atoms; arylalkoxy having 7 to 20 carbon atoms; or arylalkyl having 7 to 20 carbon atoms, $R_2$ and $R_3$ may be each independently hydrogen; alkyl having 1 to 20 carbon atoms; or aryl having 6 to 20 carbon atoms, $R_4$ to $R_9$ may be each independently hydrogen; alkyl having 1 to 20 carbon atoms; or aryl having 6 to 20 carbon atoms, and Q may be Si.

In addition, according to one embodiment of the present invention, the compound represented by Chemical Formula 1 is preferably represented by any one of the following chemical formulae:

[Chemical Formula 1-1]

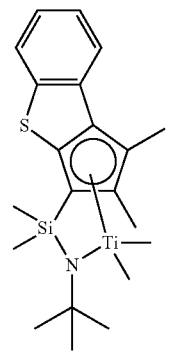

[Chemical Formula 1-2]

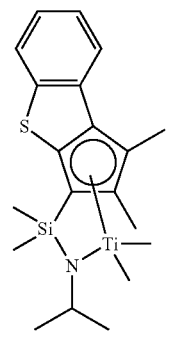

[Chemical Formula 1-3]

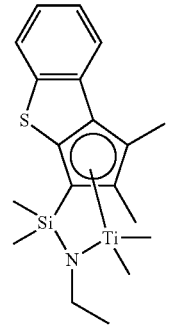

[Chemical Formula 1-4]

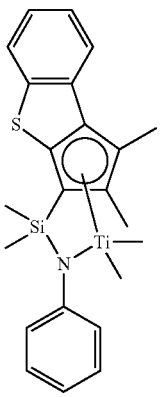

[Chemical Formula 1-5]

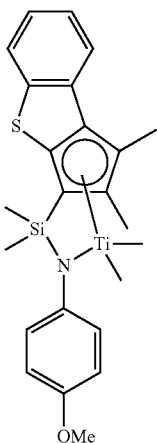

[Chemical Formula 1-6]

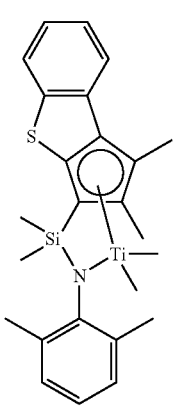

For accomplishing another object of the present invention, the present invention provides a ligand compound represented by the following Chemical Formula 2:

[Chemical Formula 2]

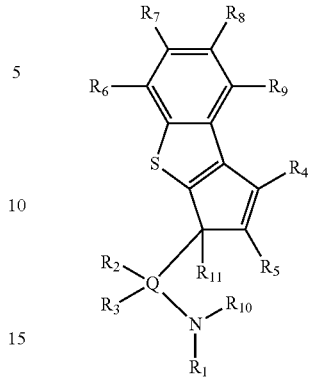

In Chemical Formula 2, $R_1$, $R_{10}$ and $R_{11}$ are each independently hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_2$ and $R_3$ are each independently hydrogen; halogen alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkylamido having 1 to 20 carbon atoms; arylamido having 6 to 20 carbon atoms; or alkylidene having 1 to 20 carbon atoms, $R_4$ to $R_9$ are each independently a metalloid radical of a group 14 metal substituted with hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or hydrocarbyl having 1 to 20 carbon atoms, two or more of $R_2$ to $R_9$ adjacent to each other may be linked to each other to form a ring, and Q may be Si, C, N, P or S.

The ligand compound of Chemical Formula 2 described in the present specification has a structure in which cyclopentadiene fused with benzothiophene through a ring-type bond, and an amido group (N—$R_1$) are stably cross-linked by Q (Si, C, N or P).

In the ligand compound, definitions of $R_1$ to $R_9$ in the compound represented by Chemical Formula 2 may be the same as the definitions in the compound represented by Chemical Formula 1, the transition metal compound.

According to the ligand compound according to one embodiment of the present invention, in Chemical Formula 2, $R_{10}$ and $R_{11}$ may be each independently hydrogen; alkyl having 1 to 20 carbon atoms; aryl having 6 to 20 carbon atoms; or alkylaryl having 6 to 20 carbon atoms.

According to one embodiment of the present invention, in Chemical Formula 2, $R_{10}$ and $R_{11}$ may be hydrogen.

According to another embodiment of the present invention, the compound represented by Chemical Formula 2 is preferably represented by any one of the following chemical formulae:

[Chemical Formula 2-1]

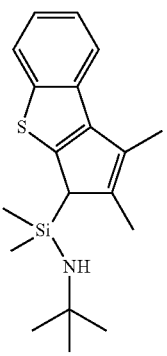

[Chemical Formula 2-2]

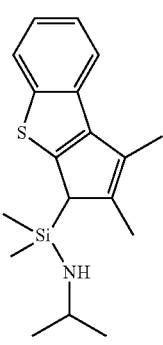

[Chemical Formula 2-3]

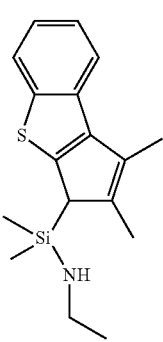

[Chemical Formula 2-4]

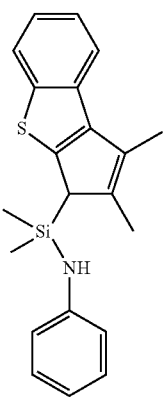

[Chemical Formula 2-5]

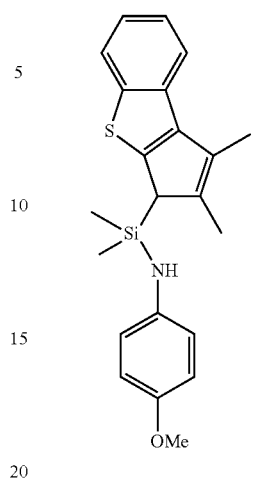

[Chemial Formula 2-6]

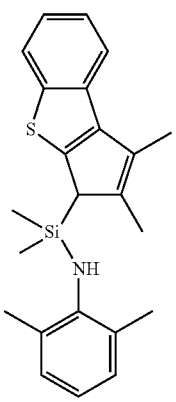

The transition metal compound of Chemical Formula 1 and the ligand compound of Chemical Formula 2 are preferably used in preparing a catalyst for polymerizing olefin monomers, however, the use is not limited thereto, and the compounds may be used in all other fields capable of using the transition metal compound.

The ligand compound represented by Chemical Formula 2 of the present invention may be prepared as in the following Reaction Formula 1.

[Reaction Formula 1]

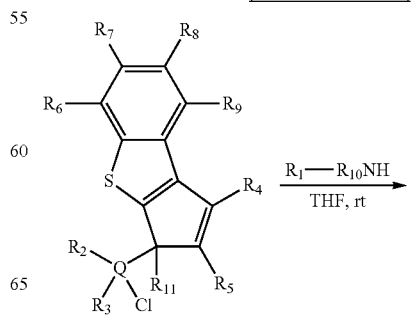

-continued

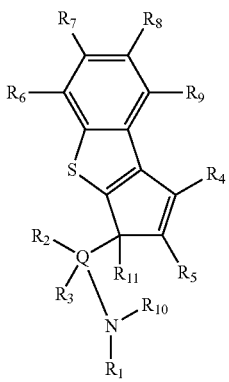

In Reaction Formula 1, $R_1$ to $R_{11}$ and Q are the same as those defined in Chemical Formula 2.

When specifically examined, the ligand compound of Chemical Formula 2 may be prepared using processes of the following a) and b):

a) a process of preparing a compound represented by the following [Chemical Formula 3] by reacting a compound represented by the following [Chemical Formula 4] with a compound represented by the following [Chemical Formula 5]; and b) a process of preparing a compound represented by the following [Chemical Formula 2] by reacting the compound represented by the following [Chemical Formula 3] with a compound represented by the following [Chemical Formula 6].

[Chemical Formula 4]

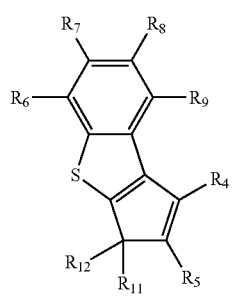

[Chemical Formula 5]

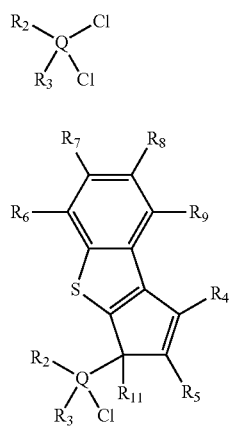

[Chemical Formula 3]

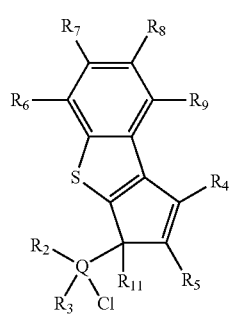

[Chemical Formula 6]

$R_1R_{10}NH$

[Chemical Formula 2]

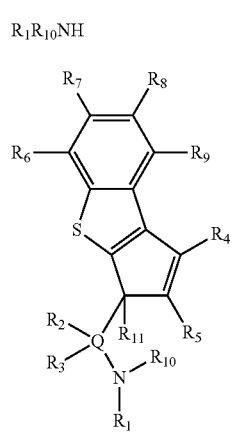

In the formulae, $R_1$ to $R_{11}$ and Q are the same as those defined in Chemical Formula 2, and $R_{12}$ is hydrogen; alkyl having 1 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms.

The transition metal compound represented by Chemical Formula 1 of the present invention may be prepared as in the following Reaction Formula 2 using the ligand compound represented by Chemical Formula 2.

[Reaction Formula 2]

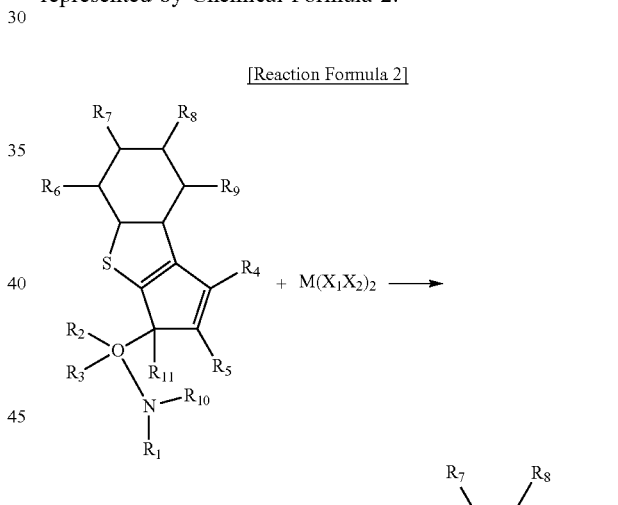

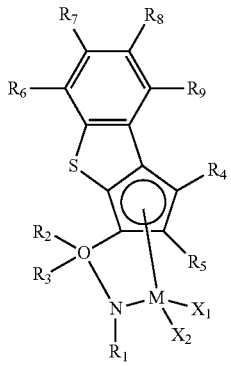

In the formula, $R_1$ to $R_{11}$, Q, M, $X_1$ and $X_2$ are the same as those defined in Chemical Formula 1 or Chemical Formula 2.

According to one embodiment of the present invention, the transition metal compound represented by Chemical Formula 1 may have a form in which a group 4 transition metal coordinately bonds with the compound represented by Chemical Formula 2 as a ligand.

When specifically examined, as in Reaction Formula 2, the transition metal compound of Chemical Formula 1 in which a group 4 transition metal coordinately bonds with the compound represented by Chemical Formula 2 as a ligand may be obtained by reacting the compound represented by Chemical Formula 2 with a compound represented by the following Chemical Formula 7, a metal precursor, and an organic lithium compound, and recrystallizing the result.

[Chemical Formula 2]

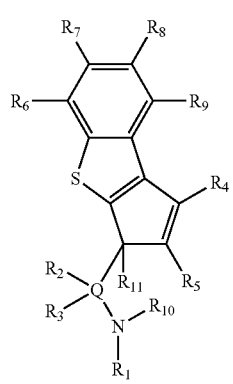

M(X$_1$X$_2$)$_2$                      [Chemical Formula 7]

[Chemical Formula 1]

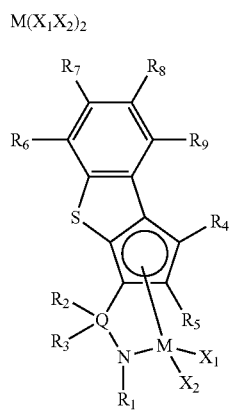

In the formulae, R$_1$ to R$_{11}$, Q, M, X$_1$ and X$_2$ are the same as those defined in Chemical Formula 1.

As examples of the organic lithium compound in Reaction Formula 2, one or more types may be selected from the group consisting of n-butyl lithium, sec-butyl lithium, methyl lithium, ethyl lithium, isopropyl lithium, cyclohexyl lithium, allyl lithium, vinyl lithium, phenyl lithium and benzyl lithium.

The compound represented by Chemical Formula 2 and the compound represented by Chemical Formula 5 are preferably mixed in a molar ratio of 1:0.8 to 1:1.5, and more preferably in a molar ratio of 1:1.0 to 1:1.1.

In addition, the organic lithium compound may be used in 180 to 250 parts by weight based on 100 parts by weight of the compound of Chemical Formula 2.

According to the preparation method according to one embodiment of the present invention, the reaction is preferably carried out for 1 hour to 48 hours in a temperature range of −80° C. to 140° C.

According to one embodiment of the present invention, the compound represented by Chemical Formula 3 and the compound represented by Chemical Formula 6 are favorably mixed in a molar ratio of 1:0.8 to 1:5.0, preferably in a molar ratio of 1:0.9 to 1:4.5, and more preferably in a molar ratio of 1:1 to 1:4.0.

In addition, according to one embodiment of the present invention, the compound represented by Chemical Formula 4 and the compound represented by Chemical Formula 5 are favorably mixed in a molar ratio of 1:0.8 to 1:5.0, preferably in a molar ratio of 1:0.9 to 1:4.0, and more preferably in a molar ratio of 1:1 to 1:3.0.

Furthermore, the reaction is preferably carried out for 1 hour to 48 hours in a temperature range of −80° C. to 140° C.

In addition, the present invention provides a catalytic composition including the compound of Chemical Formula 1.

The catalytic composition may further include a cocatalyst. As the cocatalyst, those known in the art may be used.

For example, the catalytic composition may further include at least one of the following Chemical Formulae 10 to 12 as a cocatalyst.

—[Al(R$_{22}$)—O]$_a$—                 [Chemical Formula 8]

In the formula, R$_{22}$s are each independently a halogen radical; a hydrocarbyl radical having 1 to 20 carbon atoms; or a hydrocarbyl radical having 1 to 20 carbon atoms substituted with halogen; a is an integer of 2 or greater;

D(R$_{22}$)$_3$                              [Chemical Formula 9]

In the formula, D is aluminum or boron; R$_{22}$s are each independently as defined above;

[L-H]$^+$[Z(A)$_4$]$^-$ or [L]$^+$[Z(A)$_4$]$^-$       [Chemical Formula 10]

In the formula, L is a neutral or cationic Lewis acid; H is a hydrogen atom; Z is a group 13 element; As are each independently aryl having 6 to 20 carbon atoms or alkyl having 1 to 20 carbon atoms of which one or more hydrogen atoms may be substituted with substituents; and the substituents are halogen, hydrocarbyl having 1 to 20 carbon atoms, alkoxy having 1 to 20 carbon atoms, or aryloxy having 6 to 20 carbon atoms.

As a method for preparing the catalytic composition, first, a preparation method including obtaining a mixture by bringing the transition metal compound represented by Chemical Formula 1 into contact with the compound represented by Chemical Formula 8 or Chemical Formula 9; and adding the compound represented by Chemical Formula 10 to the mixture is provided.

Second, a method for preparing the catalytic composition by bringing the transition metal compound represented by Chemical Formula 1 into contact with the compound represented by Chemical Formula 10 is provided.

In the first method of the methods for preparing the catalytic composition, a molar ratio of the compound represented by Chemical Formula 8 or Chemical Formula 9 with respect to the transition metal compound of Chemical Formula 1 is preferably 1:2 to 1:5,000, more preferably 1:10 to 1:1,000, and most preferably 1:20 to 1:500.

Meanwhile, a molar ratio of the compound represented by Chemical Formula 10 with respect to the transition metal compound of Chemical Formula 1 is preferably 1:1 to 1:25, more preferably 1:1 to 1:10, and most preferably 1:1 to 1:5.

When a molar ratio of the compound represented by Chemical Formula 8 or Chemical Formula 9 with respect to the transition metal compound of Chemical Formula 1 is less than 1:2, the amount of an alkylating agent is very small causing a problem in that alkylation of the metal compound is not completely progressed, and when the molar ratio is greater than 1:5,000, the metal compound is alkylated, however, there is a problem in that the alkylated metal compound is not fully activated due to a side reaction between the remaining excess alkylating agent and the activating agent of Chemical Formula 10. In addition, when a ratio of the compound represented by Chemical Formula 10 with respect to the transition metal compound of Chemical Formula 1 is less than 1:1, the amount of the activating agent is relatively small leading to incompletion of the metal compound activation, which causes a problem in that activity of the produced catalytic composition decreases, and when the ratio is greater than 1:25, the metal compound is fully activated, however, there is a problem in that a unit price of the catalytic composition is not economical or purity of the produced polymer declines due to the remaining excess activating agent.

In the second method of the preparation methods of a catalytic composition, a molar ratio of the compound represented by Chemical Formula 10 with respect to the transition metal compound of Chemical Formula 1 is preferably 1:1 to 1:500, more preferably 1:1 to 1:50, and most preferably 1:2 to 1:25. When the molar ratio is less than 1:1, the amount of the activating agent is relatively small leading to incompletion of the metal compound activation, which causes a problem in that activity of the produced catalytic composition decreases, and when the ratio is greater than 1:500, the metal compound is fully activated, however, there is a problem in that a unit price of the catalytic composition is not economical or purity of the produced polymer declines due to the remaining excess activating agent.

As a reaction solvent in the preparation of the composition, a hydrocarbon-based solvent such as pentane, hexane and heptane, or an aromatic-based solvent such as benzene and toluene may be used, however, the solvent is not limited thereto, and all solvents capable of being used in the art may be used.

In addition, the transition metal compound of Chemical Formula 1 and the cocatalyst may also be used in a form immersed in a carrier. As the carrier, silica or alumina may be used.

The compound represented by Chemical Formula 8 is not particularly limited as long as it is an alkyl aluminoxane. Preferable examples thereof include methyl aluminoxane, ethyl aluminoxane, isobutyl aluminoxane, butyl aluminoxane and the like, and a particularly preferable compound is methyl aluminoxane.

The compound represented by Chemical Formula 9 is not particularly limited, and preferable examples thereof include trimethyl aluminum, triethyl aluminum, triisobutyl aluminum, tripropyl aluminum, tributyl aluminum, dimethylchloroaluminum, triisopropyl aluminum, tri-s-butyl aluminum, tricyclopentyl aluminum, tripentyl aluminum, triisopentyl aluminum, trihexyl aluminum, trioctyl aluminum, ethyldimethyl aluminum, methyldiethyl aluminum, triphenyl aluminum, tri-p-tolyl aluminum, dimethylaluminummethoxide, dimethylaluminumethoxide, trimethyl boron, triethyl boron, triisobutyl boron, tripropyl boron, tributyl boron and the like, and a particularly preferable compound is selected from among trimethyl aluminum, triethyl aluminum and triisobutyl aluminum.

Examples of the compound represented by Chemical Formula 10 include triethyl ammonium tetraphenyl boron, tributyl ammonium tetraphenyl boron, trimethyl ammonium tetraphenyl boron, tripropyl ammonium tetraphenyl boron, trimethyl ammonium tetra(p-tolyl)boron, trimethyl ammonium tetra(o,p-dimethylphenyl)boron, tributyl ammonium tetra(p-trifluoromethylphenyl) boron, trimethyl ammonium tetra(p-trifluoromethylphenyl)boron, tributyl ammonium tetrapentafluorophenyl boron, N,N-diethyl anilinium tetraphenyl boron, N,N-diethyl anilinium tetraphenyl boron, N,N-diethyl anilinium tetrapentafluorophenyl boron, diethyl ammonium tetrapentafluorophenyl boron, triphenyl phosphonium tetraphenyl boron, trimethyl phosphonium tetraphenyl boron, triethyl ammonium tetraphenyl aluminum, tributyl ammonium tetraphenyl aluminum, trimethyl ammonium tetraphenyl aluminum, tripropyl ammonium tetraphenyl aluminum, trimethyl ammonium tetra(p-tolyl)aluminum, tripropyl ammonium tetra(p-tolyl)aluminum, triethyl ammonium tetra(o,p-dimethylphenyl)aluminum, tributyl ammonium tetra(p-trifluoromethylphenyl)aluminum, trimethyl ammonium tetra(p-trifluoromethylphenyl)aluminum, tributyl ammonium tetrapentafluorophenyl aluminum, N,N-diethyl anilinium tetraphenyl aluminum, N,N-diethyl anilinium tetraphenyl aluminum, N,N-diethyl anilinium tetrapentafluorophenyl aluminum, diethyl ammonium tetrapentatetraphenyl aluminum, triphenyl phosphonium tetraphenyl aluminum, trimethyl phosphonium tetraphenyl aluminum, triethyl ammonium tetraphenyl aluminum, tributyl ammonium tetraphenyl aluminum, trimethyl ammonium tetraphenyl boron, tripropyl ammonium tetraphenyl boron, trimethyl ammonium tetra(p-tolyl)boron, tripropyl ammonium tetra(p-tolyl)boron, triethyl ammonium tetra(o,p-dimethylphenyl)boron, trimethyl ammonium tetra(o,p-dimethylphenyl)boron, tributyl ammonium tetra(p-trifluoromethylphenyl) boron, trimethyl ammonium tetra(p-trifluoromethylphenyl)boron, tributyl ammonium tetrapentafluorophenyl boron, N,N-diethyl anilinium tetraphenyl boron, N,N-diethyl anilinium tetraphenyl boron, N,N-diethyl anilinium tetrapentafluorophenyl boron, diethyl ammonium tetrapentafluorophenyl boron, triphenyl phosphonium tetraphenyl boron, triphenyl carbonium tetra(p-trifluoromethylphenyl)boron, triphenyl carbonium tetrapentafluorophenyl boron and the like.

A polyolefin homopolymer or copolymer may be prepared by bringing a catalytic composition including the transition metal compound of Chemical Formula 1; and one or more compounds selected from among the compounds represented by Chemical Formula 8 to Chemical Formula 10 into contact with one or more olefin monomers.

A most preferable preparation process using the catalytic composition is a solution process, and in addition thereto, a slurry or vapor process may also be used when such a composition is used with an inorganic carrier such as silica.

In the preparation process, the activated catalytic composition may be injected by being dissolved or diluted in an aliphatic hydrocarbon solvent having 5 to 12 carbon atoms such as pentane, hexane, heptane, nonane, decane, and isomers thereof, an aromatic hydrocarbon solvent such as toluene benzene, a hydrocarbon solvent substituted with a chlorine atom such as dichloromethane and chlorobenzene, and the like, which are suited for an olefin polymerization process. The solvent used herein is preferably treated with a small amount of an alkyl aluminum to remove a small quantity of water or air that acts as a catalytic poison, and then used, and carrying out by further using a cocatalyst is also possible.

Examples of the olefin-based monomer capable of being polymerized with the metal compounds and a cocatalyst include ethylene, alpha-olefin, cyclic olefin and the like, and diene olefin-based monomers or triene olefin-based monomers and the like having two or more double bonds may also be polymerized. Specific examples of the monomer include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-icosene, norbornene, norbornadiene, ethylidene norbornene, phenyl norbornene, vinyl norbornene, dicyclopentadiene, 1,4-butadiene, 1,5-pentadiene, 1,6-hexadiene, styrene, alpha-methyl styrene, divinylbenzene, 3-chloromethyl styrene and the like, and two or more types of these monomers may be mixed and copolymerized.

Particularly, the catalytic composition in the preparation method of the present invention is capable of preparing a very low-density copolymer having polymer density of 0.89 g/cc or less while having a high molecular weight in a copolymerization reaction of a monomer with high steric hindrance such as ethylene and 1-octene even at a higher reaction temperature of 90° C. or higher.

According to one embodiment of the present invention, a polymer prepared using the preparation method of the present invention has density of less than 0.891 g/cc.

According to one embodiment of the present invention, a polymer prepared using the preparation method of the present invention has density of 0.88 g/cc or less.

According to one embodiment of the present invention, a polymer prepared using the preparation method of the present invention has density of less than 0.87 g/cc.

In addition, according to one embodiment of the present invention, when a polymer is formed using the transition metal catalyst of Chemical Formula 1, the polymer may have a single Tm (melting temperature) peak or two Tm peaks.

Tm may be obtained using a differential scanning calorimeter 6000 (DSC) manufactured by PerkinElmer, and may be measured with the top of the DSC curve as a melting point (melting temperature) after raising the temperature of a polymer to 100° C., maintaining the temperature for 1 minute, then lowering the temperature to −100° C., and raising the temperature again.

According to one embodiment of the present invention, a polymer prepared using the preparation method of the present invention has Tm of 92 or less.

According to one embodiment of the present invention, Tm of a polymer prepared using the preparation method of the present invention may exhibit one or two peaks.

According to one embodiment of the present invention, a polymer prepared using the preparation method of the present invention has a melt index (Mi) of less than 4.

According to one embodiment of the present invention, a polymer prepared using the preparation method of the present invention has a melt index (Mi) of 2 or less.

According to one embodiment of the present invention, a polymer prepared using the preparation method of the present invention has a melt index (Mi) of 1 or less.

When the melt index according to the embodiments of the present invention is low of less than 2, a high molecular weight polymer may be produced, and particularly, the polymer is useful as a multilayer film for coating requiring a high molecular weight polymer.

Hereinafter, the present invention will be described in more detail with reference to the following examples. However, these examples are for illustrative purposes only, and the scope of the present invention is not limited thereto.

Synthesis of Ligand and Transition Metal Compound

Organic reagents and solvents were purchased from Aldrich and purified using a standard method to be used unless particularly mentioned otherwise. Contact with air and moisture was blocked in all synthesis steps in order to enhance the reproducibility of experiments. A compound substituted with tetramethyl cyclobutadiene among ketone compounds in Chemical Formula 1 was synthesized according to a literature [*Organometallics* 2002, 21, 2842-2855], and CGC [Me$_2$Si(Me$_4$C$_5$)NtBu]TiMel$_2$ (Constrained-Geometry Catalyst, abbreviated as CGC hereinafter) of Comparative Example 1 was synthesized according to U.S. Pat. No. 6,015,916.

Preparation of Ligand Compound

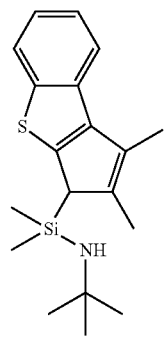

[Chemical Formula 2-1]

Synthesis of N-tert-butyl-1-(1,2-dimethyl-3H-benzo[b]cyclopenta[d]thiophen-3-yl)-1,1-dimethylsilanamine After 4.65 g (15.88 mmol) of a compound of Chemical Formula 3 was quantitated and added to a 100 ml schlenk flask, 80 ml of THF was introduced thereto. After introducing tBuNH$_2$ (4 eq, 6.68 ml) thereto at room temperature, the result was reacted for 3 days at room temperature. After the reaction, THF was removed, and the result was filtered using hexane. The solvent was dried, and a yellow liquid was obtained in a yield of 4.50 g (86%).

$^1$H-NMR (in CDCl$_3$, 500 MHz):
7.99 (d, 1H), 7.83 (d, 1H), 7.35 (dd, 1H), 7.24 (dd, 1H), 3.49 (s, 1H), 2.37 (s, 3H), 2.17 (s, 3H), 1.27 (s, 9H), 0.19 (s, 3H), −0.17 (s, 3H).

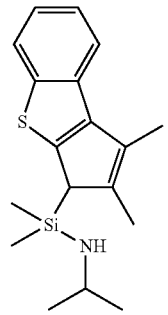

[Chemical Formula 2-2]

Synthesis of 1-(1,2-dimethyl-3H-benzo[b]cyclopenta[d]thiophen-3-yl)-N-isopropyl-1,1-dimethylsilanamine After 1.00 g (3.44 mmol) of a compound of Chemical Formula 3 was quantitated and added to a 100 ml schlenk flask, 25 ml of THF was introduced thereto. The schlenk flask was immersed in a −78° C. low-temperature bath made of dry ice and acetone, and stirred for 30 minutes. Subsequently, isopropylamine (0.4 g, 6.88 mmol) was dissolved in THF (7 ml), and the result was slowly introduced to the flask under argon. The result was stirred for 1 hour at −78° C., and then stirred while slowly raising the temperature to room temperature. Next, the result was filtered using diethyl ether, the filtrate was taken and the solvent was dried to obtain a yellow liquid in a yield of 597.0 mg (55%).

$^1$H-NMR (in $C_6D_6$, 500 MHz):

7.98 (d, 2H), 7.72 (d, 1H), 7.24 (dd, 1H), 7.10 (dd, 1H), 3.23 (s, 1H), 2.89-2.83 (m, 1H), 2.25 (s, 3H), 2.00 (s, 3H), 0.98 (d, 3H), 0.92 (d, 3H), 0.05 (s, 3H), −0.14 (s, 3H).

[Chemical Formula 2-3]

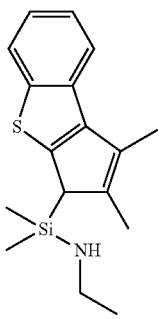

Synthesis of 1-(1,2-dimethyl-3H-benzo[b]cyclopenta[d]thiophen-3-yl)-N-ethyl-1,1-dimethylsilanamine After 1.40 g (4.78 mmol) of a compound of Chemical Formula 3 was quantitated and added to a 100 ml schlenk flask, 30 ml of THF was introduced thereto. After introducing tBuNH$_2$ (2 eq, 4.78 ml, 2.0 M in THF) thereto at room temperature, the result was reacted for 3 hours at room temperature. After the reaction, THF was removed, and then the result was filtered using hexane. The solvent was dried, and a yellow liquid was obtained in a yield of 1.41 g (98%).

$^1$H-NMR (in CDCl$_3$, 500 MHz):

7.99 (d, 1H), 7.83 (d, 1H), 7.36 (dd, 1H), 7.24 (dd, 1H), 3.49 (s, 1H), 2.84 (m, 2H), 2.37 (s, 3H), 2.16 (s, 3H), 1.11 (t, 3H), 0.09 (s, 3H), −0.09 (s, 3H).

[Chemical Formula 2-4]

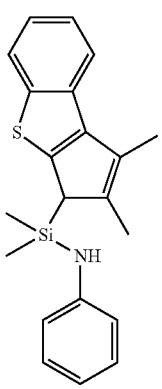

Synthesis of 1-(1,2-dimethyl-3H-benzo[b]cyclopenta[d]thiophen-3-yl)-1,1-dimethyl-N-phenylsilanamine Aniline (1.47 g, 5.12 mmol) and THF (25 ml) were mixed and stirred in a 250 ml schlenk flask. The schlenk flask was immersed in a −78° C. low-temperature bath made of dry ice and acetone, and stirred for 30 minutes. Subsequently, n-BuLi (1.36 ml, 2.5 M, 3.41 mmol) was slowly added dropwise thereto. At this point, the color of the reaction mixture slowly turned to yellow. The result was stirred for 1 hour while gradually raising the temperature to room temperature. In another schlenk flask, Chemical Formula 3 (1.0 g, 3.41 mmol) and THF (20 ml) were mixed and stirred. This schlenk flask was immersed in a −78° C. low-temperature bath made of dry ice and acetone, and stirred for 30 minutes. Next, the reaction solution in the schlenk flask was slowly added dropwise to this schlenk flask. The result was stirred while gradually raising the temperature to room temperature. Next, all the solvent was removed, and the result was filtered using diethyl ether, the filtrate was taken and the solvent was dried. As a result an orange liquid was obtained in a yield of 692.0 mg (58%).

$^1$H-NMR (in $C_6D_3$, 500 MHz):

7.93 (d, 1H), 7.65 (d, 1H), 7.21 (dd, 1H), 7.13 (dd, 2H), 7.06 (dd, 1H), 6.78 (dd, 1H), 6.59 (dd, 2H), 3.51 (s, 1H), 3.13 (br, 1H), 2.16 (s, 3H), 1.88 (s, 3H), 0.07 (s, 3H), −0.15 (s, 3H).

[Chemical Formula 2-5]

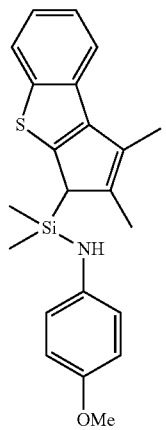

Synthesis of 1-(1,2-dimethyl-3H-benzo[b]cyclopenta[d]thiophen-3-yl)-N-(4-methoxyphenyl)-1,1-dimethylsilanamine Anisidine (1.02 g, 8.25 mmol) and THF (20 ml) were mixed and stirred in a 250 ml schlenk flask. The schlenk flask was immersed in a −78° C. low-temperature bath made of dry ice and acetone, and stirred for 30 minutes. Subsequently, n-BuLi (2.20 ml, 2.5 M, 5.50 mmol) was slowly added dropwise thereto, and the result was stirred for 1 hour while raising the temperature to room temperature. In another schlenk flask, Chemical Formula 3 (1.61 g, 5.50 mmol) and THF (20 ml) were mixed and stirred. This schlenk flask was immersed in a −78° C. low-temperature bath made of dry ice and acetone, and stirred for 30 minutes. Next, the reaction solution in the schlenk flask was slowly added dropwise to this schlenk flask. The result was stirred while gradually raising the temperature to room temperature. Next, all the solvent was removed, and the result was filtered using diethyl ether, the filtrate was taken and the solvent was dried. As a result an orange liquid was obtained in a yield of 1.15 g (55%).

$^1$H-NMR (in CDCl$_3$, 500 MHz):

7.96 (d, 1H), 7.69 (d, 1H), 7.24 (dd, 1H), 7.09 (dd, 1H), 6.78 (m, 2H), 6.56 (m, 2H), 3.55 (s, 1H), 3.39 (s, 3H), 2.97 (br, 1H), 2.21 (s, 3H), 1.94 (s, 3H), 0.10 (s, 3H), −0.08 (s, 3H).

[Chemical Formula 2-6]

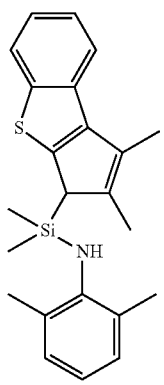

Synthesis of 1-(1,2-dimethyl-3H-benzo[b]cyclopenta[d]thiophen-3-yl)-N-(2,6-dimethylphenyl)-1,1-dimethylsilanamine 2,6-Dimethylaniline (0.45 ml, 3.66 mmol) and THF (25 ml) were mixed and stirred in a 250 ml schlenk flask. The schlenk flask was immersed in a −78° C. low-temperature bath made of dry ice and acetone, and stirred for 30 minutes. Subsequently, n-BuLi (0.98 ml, 2.5 M, 2.44 mmol) was slowly added dropwise thereto, and the result was stirred for 1 hour while gradually raising the temperature to room temperature. In another schlenk flask, Chemical Formula 3 (720.0 mg, 2.44 mmol) and THF (20 ml) were mixed and stirred. This schlenk flask was immersed in a −78° C. low-temperature bath made of dry ice and acetone, and stirred for 30 minutes. Next, the reaction solution in the schlenk flask was slowly added dropwise to this schlenk flask. The result was stirred while gradually raising the temperature to room temperature. Next, all the solvent was removed, and the result was filtered using diethyl ether, the filtrate was taken and the solvent was dried. As a result an orange liquid was obtained in a yield of 636.0 mg (69%).

$^1$H-NMR (in C$_6$D$_6$, 500 MHz):

7.97 (d, 1H), 7.69 (d, 1H), 7.26 (dd, 1H), 7.10 (dd, 1H), 6.93 (d, 2H), 6.85 (dd, 1H), 3.26 (s, 1H), 2.91 (br, 1H), 2.21 (s, 3H), 1.94 (s, 3H), 1.87 (s, 6H), 0.07 (s, 3H), −0.05 (s, 3H).

Preparation of Transition Metal Compound

Example 1

Chemical Formula 1-1

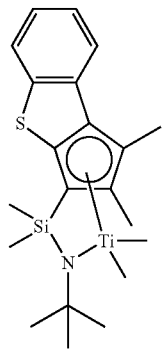

In a 50 ml schlenk flask, the ligand compound of Chemical Formula 2-1 (1.06 g, 3.22 mmol/1.0 eq) and 16.0 mL (0.2 M) of MTBE were placed, and stirred first. At −40° C., n-BuLi (2.64 ml, 6.60 mmol/2.05 eq, 2.5 M in THF) was added thereto, and the result was reacted overnight at room temperature. After that, MeMgBr (2.68 ml, 8.05 mmol/2.5 eq, 3.0 M in diethyl ether) was slowly added dropwise thereto at −40° C., and then TiCl$_4$ (2.68 ml, 3.22 mmol/1.0 eq, 1.0 M in toluene) was added in order, and the result was reacted overnight at room temperature. After that, the reaction mixture was filtered by passing through Celite using hexane. After the solvent was dried, a brown solid was obtained in a yield of 1.07 g (82%).

$^1$H-NMR (in CDCl$_3$, 500 MHz):

7.99 (d, 1H), 7.68 (d, 1H), 7.40 (dd, 1H), 7.30 (dd, 1H), 3.22 (s, 1H), 2.67 (s, 3H), 2.05 (s, 3H), 1.54 (s, 9H), 0.58 (s, 3H), 0.57 (s, 3H), 0.40 (s, 3H), −0.45 (s, 3H).

Example 2

Chemical Formula 1-2

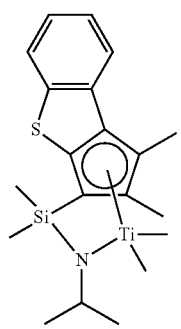

In a 10 ml schlenk flask, the ligand compound of Chemical Formula 2-2 (134.0 mg, 0.43 mmol/1.0 eq) and 2.6 mL (0.2 M) of MTBE were placed and stirred. At −40° C., n-BuLi (0.34 ml, 0.86 mmol/2.0 eq, 2.5 M in THF) was added thereto, and the result was reacted overnight at room temperature. After that, MeMgBr (0.85 ml, 1.3 mmol/3.0 eq, 3.0 M in diethyl ether) was slowly added dropwise thereto at −40° C., and then TiCl$_4$ (0.43 ml, 0.43 mmol/1.0 eq, 1.0 M in toluene) was added in order, and the result was reacted overnight at room temperature. After that, the reaction mixture was filtered by passing through Celite using hexane. After the solvent was dried, a brown solid was obtained in a yield of 60.6 mg (36%).

$^1$H-NMR (in $C_6D_6$, 500 MHz):

7.80 (d, 1H), 7.39 (d, 1H), 7.17 (dd, 1H), 7.01 (dd, 1H), 5.02 (m, 1H), 2.36 (s, 3H), 1.89 (s, 3H), 1.22 (m, 6H), 0.61 (s, 3H), 0.58 (s, 3H), 0.40 (s, 3H), −0.03 (s, 3H).

Example 3

Chemical Formula 1-3

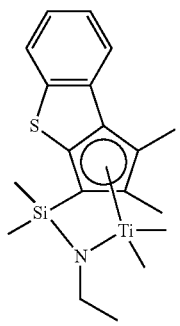

In a 50 ml schlenk flask, the ligand compound of Chemical Formula 2-3 (1.45 g, 4.81 mmol/1.0 eq) and 25 mL (0.2 M) of MTBE were placed and stirred. At −40° C., n-BuLi (3.94 ml, 9.86 mmol/2.5 eq, 2.5 M in THF) was added thereto, and the result was reacted overnight at room temperature. After that, MeMgBr (4.0 ml, 12.02 mmol/2.5 eq, 3.0 M in diethyl ether) was slowly added dropwise thereto at −40° C., and then TiCl$_4$ (4.81 ml, 4.81 mmol/1.0 eq, 1.0 M in toluene) was added in order, and the result was reacted overnight at room temperature. The reaction was not complete based on an NMR result, and MeLi (3.0 ml, 4.81 mmol/1.0 eq, 1.6 M in diethyl ether) was slowly added dropwise thereto to complete the reaction. After that, the reaction mixture was filtered by passing through Celite using hexane. After the solvent was dried, a brown solid was obtained in a yield of 1.02 g (56%).

$^1$H-NMR (in CDCl$_3$, 500 MHz):

8.03 (d, 1H), 7.68 (d, 1H), 7.42 (dd, 1H), 7.30 (dd, 1H), 4.23 (q, 2H), 2.70 (s, 3H), 2.08 (s, 3H), 1.30 (t, 3H), 0.83 (s, 3H), 0.54 (s, 3H), 0.53 (s, 3H), 0.35 (s, 3H), 0.09 (s, 3H), −0.46 (s, 3H).

Example 4

Chemical Formula 1-4

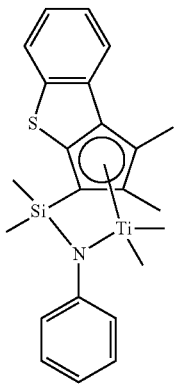

In a 10 ml schlenk flask, the ligand compound of Chemical Formula 2-4 (388.6 mg, 1.11 mmol/1.0 eq) and 5.6 mL (0.2 M) of MTBE were placed and stirred. At −40° C., n-BuLi (0.89 ml, 2.22 mmol/2.0 eq, 2.5 M in THF) was added thereto, and the result was reacted overnight at room temperature. After that, MeMgBr (1.11 ml, 3.33 mmol/3.0 eq, 3.0 M in diethyl ether) was slowly added dropwise thereto at −40° C., and then TiCl$_4$ (1.11 ml, 1.11 mmol/1.0 eq, 1.0 M in toluene) was added in order, and the result was reacted overnight at room temperature. After that, the reaction mixture was filtered by passing through Celite using hexane. After the solvent was dried, a brown solid was obtained in a yield of 175.0 mg (37%).

$^1$H-NMR (in $C_6D_6$, 500 MHz):

7.76 (d, 1H), 7.39 (d, 1H), 7.26 (m, 4H), 7.18 (m, 1H), 7.01 (dd, 1H), 6.92 (dd, 1H), 2.33 (s, 3H), 1.94 (s, 3H), 0.85 (s, 3H), 0.62 (s, 3H), 0.43 (s, 3H), 0.23 (s, 3H).

Example 5

Chemical Formula 1-5

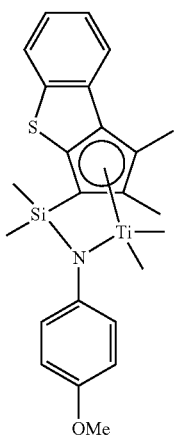

In a 10 ml schlenk flask, the ligand compound of Chemical Formula 2-5 (242.0 mg, 0.64 mmol/1.0 eq) and 3.2 mL (0.2 M) of MTBE were placed and stirred. At −40° C., n-BuLi (0.51 ml, 1.28 mmol/2.0 eq, 2.5 M in THF) was added thereto, and the result was reacted overnight at room temperature. After that, MeMgBr (0.64 ml, 1.92 mmol/3.0 eq, 3.0 M in diethyl ether) was slowly added dropwise thereto at −40° C., and then TiCl$_4$ (0.64 ml, 0.64 mmol/1.0 eq, 1.0 M in toluene) was added in order, and the result was reacted overnight at room temperature. After that, the reaction mixture was filtered by passing through Celite using hexane. After the solvent was dried, a brown solid was obtained in a yield of 152.0 mg (52%).

$^1$H-NMR (in C$_6$D$_6$, 500 MHz):

7.78 (d, 1H), 7.41 (d, 1H), 7.19-6.84 (m, 6H), 3.34 (s, 3H), 3.35 (s, 3H), 1.98 (s, 3H), 0.83 (s, 3H), 0.63 (s, 3H), 0.44 (s, 3H), 0.21 (s, 3H).

Example 6

Chemical Formula 1-6

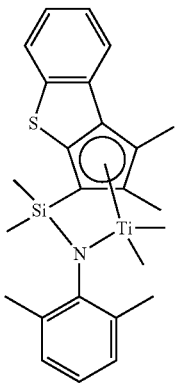

In a 10 ml schlenk flask, the ligand compound of Chemical Formula 2-6 (116.0 mg, 0.31 mmol/1.0 eq) and 2.0 mL (0.2 M) of MTBE were placed and stirred. At −40° C., n-BuLi (0.25 ml, 0.61 mmol/2.0 eq, 2.5 M in THF) was added thereto, and the result was reacted overnight. After that, MeMgBr (0.31 ml, 0.93 mmol/3.0 eq, 3.0 M in diethyl ether) was slowly added dropwise thereto at −40° C., and then TiCl$_4$ (0.31 ml, 0.31 mmol/1.0 eq, 1.0 M in toluene) was added in order, and the result was reacted overnight at room temperature. After that, the reaction mixture was filtered by passing through Celite using hexane. After the solvent was dried, a brown solid was obtained in a yield of 79.0 mg (56%).

$^1$H-NMR (in C$_6$D$_6$, 500 MHz):

7.74 (d, 1H), 7.37 (d, 1H), 7.19-6.97 (m, 5H), 2.32 (s, 3H), 2.26 (s, 3H), 2.25 (s, 3H), 2.03 (s, 3H), 0.67 (s, 3H), 0.55 (s, 3H), 0.34 (s, 3H), 0.05 (s, 3H).

Comparative Example 1

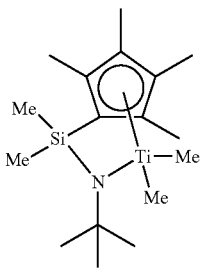

Synthesis of (tert-butyl(dimethyl(2,3,4,5-tetramethylcyclopenta-2,4-dien-1-yl)silyl)amino)dimethyltitanium In a 100 ml schlenk flask, the ligand compound of the comparative example (2.36 g, 9.39 mmol/1.0 eq) and 50 mL (0.2 M) of MTBE were placed and stirred. At −40° C., n-BuLi (7.6 ml, 19.25 mmol/2.05 eq, 2.5 M in THF) was added thereto, and the result was reacted overnight at room temperature. After that, MeMgBr (6.4 ml, 19.25 mmol/2.05 eq, 3.0 M in diethyl ether) was slowly added dropwise thereto at −40° C., and then TiCl$_4$ (9.4 ml, 9.39 mmol/1.0 eq, 1.0 M in toluene) was added in order, and the result was reacted overnight at room temperature. After that, the reaction mixture was filtered by passing through Celite using hexane. After the solvent was dried, a yellow solid was obtained in a yield of 2.52 g (82%).

$^1$H-NMR (in CDCl$_3$, 500 MHz):

2.17 (s, 6H), 1.92 (s, 6H), 1.57 (s, 9H), 0.48 (s, 6H), 0.17 (s, 6H).

Preparation Example of Polymer

Example 1 (Examples 1-1 to 1-4) to Example 6, and Comparative Example 1

After adding a hexane solvent (1.0 L) and 1-octene (210 ml) to a 2 L autoclave reactor, the reactor was preheated to a temperature of 150° C. At the same time, a pressure of the reactor was filled with ethylene (35 bar) in advance. A dimethyl anilinium tetrakis (pentafluorophenyl)borate cocatalyst (20 µmol) and a compound of the second column (2.0 µmol) of the following Table 1 treated with a triisobutyl aluminum compound were consequently added to the reactor with adding a high argon pressure (molar ratio of Al:Ti=10:1). Subsequently, a copolymerization reaction was progressed for 8 minutes. Next, the remaining ethylene gas was released, and the polymer solution was added to excess ethanol to induce precipitation. The precipitated polymer was washed twice to three times with ethanol, dried for 12 hours or longer in a vacuum oven at 90° C., and physical properties of the polymer were measured.

Various polymers were prepared depending on polymerization temperatures, main catalysts and cocatalysts of the following Table 1, and the results are shown in Tables 1 and 2.

Physical Property Evaluation (Weight, Activity, Melt Index, Melting Point, Density)

<Melt Index of Polymer>

Melt indexes (MI) of the polymers were measured in reference with the ASTM D-1238 (condition E, 190° C., 2.16 Kg load).

<Melting Temperature of Polymer>

Melting temperatures (Tm) of the polymers may be obtained using a differential scanning calorimeter 6000 (DSC) manufactured by PerkinElmer, and the melting temperatures of the polymer may be measured such that the measurement container is filled with approximately 0.5 mg to 10 mg of the sample, nitrogen gas flow is set at 20 ml/min, and after the sample is heated from 0° C. to a temperature of 150° C. at a rate of 20° C./min in order to have the same thermal history of the polyolefin resin, the sample is cooled again from 150° C. to a temperature of −100° C. at a rate of 10° C./min, and the melting temperature is measured while heating the sample again from −100° C. to a temperature of 150° C. at a rate of 10° C./min with a heating curve peak of heat flow measured with a DSC, that is, an endothermic peak temperature during the heating as a melting temperature.

<Density of Polymer>

Density of the polymers was measured in a Mettler scale after preparing the sample to a sheet having a thickness of 3 mm and a radius of 2 cm using 190° C. press mold, and then annealing the sheet for 24 hours at room temperature.

Physical properties of the polymers prepared in Example 1 (Examples 1-1 to 1-4) and Comparative Example 1 are shown in the following Table 1.

<Measurement on Readiness of Low Density and High Molecular Weight Product Depending on Temperature>

TABLE 1

| Cat. | Cat. | Polymerization Temperature (° C.) | Cocat. | Yield (g) | Density (g/cc) | Melt Index (MI) (g/10 min) | Tm (° C.) |
|---|---|---|---|---|---|---|---|
| Comparative Example 1 | CGC | 150 | AB | 45.4 | 0.900 | 13.8 | 102.4 |
| Example 1-1 | Chemical Formula 1-1 | 150 | AB | 48.1 | 0.891 | 0.61 | 88.6 |
| Example 1-2 | Chemical Formula 1-1 | 150 | TB | 45.8 | 0.893 | 0.005 | 90.4 |
| Example 1-3 | Chemical Formula 1-1 | 120 | AB | 76.1 | 0.894 | 0.47 | 89.2 |
| Example 1-4 | Chemical Formula 1-1 | 120 | TB | 75.6 | 0.894 | 0.016 | 91.5 |

Polymerization condition: hexane (1.0 L), ethylene (35 bar), Cocat.: 10 equiv, 1-C8 210 ml,
t = 8 min
AB: dimethyl anilinium tetrakis(pentafluorophenyl)borate cocatalyst
TB: triisobutyl aluminum compound As shown in Table 1, it was identified that lower density and a higher molecular weight were obtained at 150° C. in Example 1 of the present invention compared to the comparative example. It was identified that, in the polymerization at 120° C., the yield significantly increased although basic physical properties were similar.

In addition, in Comparative Example 1, density was high of 0.900 g/cc, and MI was 13 or greater, thus, preparing a high molecular weight product may be difficult, however, when a melt index (MI) was low as in Example 1 of the present invention, a high molecular weight product may be prepared.

Furthermore, it was identified that 0.891 to 0.894 g/cc and a melt index of 0.61 g/10 min or less were capable of being maintained when using different cocatalysts, or lowering a polymerization temperature.

In the polymers of Examples 1-1 to 1-4, the melt index was 0.005 g/10 min compared to Comparative Example 1, and it was identified that the melt index was capable of being significantly decreased by 25 times or greater compared to Comparative Example 1.

<Measurement on Preparation Readiness of High Molecular Weight Elastomer Depending on Density and Melt Index>

TABLE 2

| Cat. | Polymerization Temperature (° C.) | Cocat. | Yield (g) | Density (g/cc) | Melt Index (MI) (g/10 min) | Tm (° C.) |
|---|---|---|---|---|---|---|
| Comparative Example 1 | 150 | AB | 45.4 | 0.900 | 13.8 | 102.4 |
| Example 1 | 150 | AB | 48.1 | 0.891 | 0.61 | 88.6 |
| Example 2 | 150 | AB | 47.6 | 0.876 | 0.37 | (55.5)/89.4 |
| Example 3 | 150 | AB | 21.5 | 0.869 | 0.52 | 46.0/87.2 |
| Example 4 | 150 | AB | 26.5 | 0.861 | 2.79 | 39.1 |
| Example 5 | 150 | AB | 22.7 | 0.863 | 3.50 | 46.8 |

Polymerization condition: hexane (1.0 L), ethylene (35 bar), Cocat.: AB 10 equiv, 1-C8 210 ml,
t = 8 min As examined in Table 2, it was seen that, when forming a polymer using the transition metal compounds prepared in Examples 1 to 5, the density and the melt index were significantly lower compared to Comparative Example 1.

When specifically examined, it was seen that, when forming a polymer using the transition metal compounds prepared in Examples 1 to 5, the density of the polymer decreased compared to the case using Comparative Example 1. For example, the density of the polymer was from 0.862 g/cc to 0.891 g/cc and a low density value was capable of being obtained when forming a polymer using the transition metal compounds prepared in Examples 1 to 5, while the density was 0.900 g/cc or greater in Comparative Example 1.

In addition, as for the melt index, the melt index of the polymer was from 0.37 to 3.50 (g/10 min) when forming a polymer using the transition metal compounds prepared in Examples 1 to 5, and particularly, it was seen that the melt index decreased by 30 times or greater compared to Comparative Example 1 when forming a polymer using the transition metal compounds prepared in Examples 1 to 5. The melt index being low means that a high molecular weight polymer is capable of being produced.

Accordingly, when forming a polymer using the transition metal compounds prepared in Examples 1 to 5, the compound according to the present invention is capable of producing a polymer of a low density area and a polymer of a high molecular weight having excellent copolymerizability.

What is claimed is:

1. A transition metal compound represented by the following Chemical Formula 1:

[Chemical Formula 1]

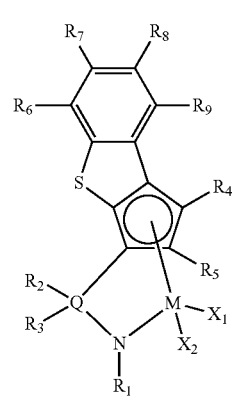

wherein, in Chemical Formula 1, $R_1$ is hydrogen; alkyl having 1 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms;

$R_2$ and $R_3$ are each independently hydrogen; alkyl having 1 to 20 carbon atoms; aryl having 6 to 20 carbon atoms; or alkylaryl having 6 to 20 carbon atoms;

$R_4$ to $R_9$ are each independently hydrogen; alkyl having 1 to 20 carbon atoms; aryl having 6 to 20 carbon atoms; alkylaryl having 7 to 20 carbon atoms; or arylalkyl having 7 to 20 carbon atoms;

two or more of $R_2$ and $R_3$; $R_4$ and $R_5$; $R_6$ and $R_7$; $R_7$ and $R_8$; and $R_8$ and $R_9$ are optionally linked to each other to form a ring;

Q is Si;

M is a group 4 transition metal; and $X_1$ and $X_2$ are each independently hydrogen, halogen, alkyl having 1 to 20 carbon atoms, alkenyl having 2 to 20 carbon atoms, aryl having 6 to 20 carbon atoms, alkylaryl having 7 to 20 carbon atoms, arylalkyl having 7 to 20 carbon atoms, alkylamino having 1 to 20 carbon atoms, arylamino having 6 to 20 carbon atoms or alkylidene having 1 to 20 carbon atoms.

2. The transition metal compound of claim 1, wherein, in Chemical Formula 1, $R_1$ is alkyl having 1 to 20 carbon atoms; aryl having 6 to 20 carbon atoms; arylalkoxy having 7 to 20 carbon atoms; or arylalkyl having 7 to 20 carbon atoms;

$R_2$ and $R_3$ are each independently hydrogen; alkyl having 1 to 20 carbon atoms; or aryl having 6 to 20 carbon atoms;

$R_4$ to $R_9$ are each independently hydrogen; alkyl having 1 to 20 carbon atoms; or aryl having 6 to 20 carbon atoms; and Q is Si.

3. The transition metal compound of claim 2, wherein M is Ti, Hf or Zr.

4. The transition metal compound of claim 3, wherein the compound represented by Chemical Formula 1 is represented by any one of the following chemical formulae:

[Chemical Formula 1-1]

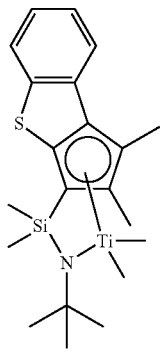

[Chemical Formula 1-2]

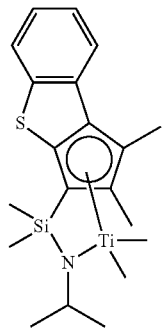

[Chemical Formula 1-3]

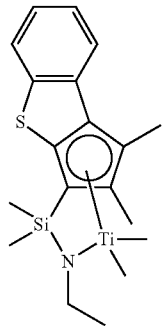

[Chemical Formula 1-4]

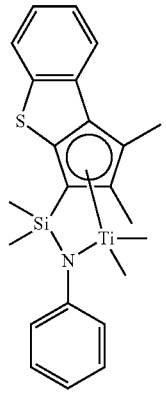

[Chemical Formula 1-5]

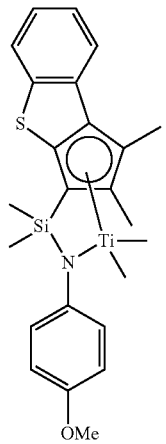

-continued

[Chemical Formula 1-6]

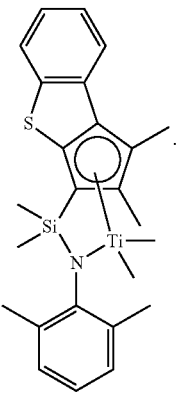

5. A catalytic composition comprising the transition metal compound of claim 1.

6. The catalytic composition of claim 5, further comprising one or more cocatalysts, wherein the cocatalyst includes one or more selected from among the following Chemical Formulae 8 to 10:

$$—[Al(R_{22})-O]_a-$$ [Chemical Formula 8]

wherein, in the formula, each $R_{22}$ represents independently a halogen radical; a hydrocarbyl radical having 1 to 20 carbon atoms; or a hydrocarbyl radical having 1 to 20 carbon atoms substituted with halogen; a is an integer of 2 or greater;

$$D(R_{22})_3$$ [Chemical Formula 9]

wherein, in the formula, D is aluminum or boron; each $R_{22}$ represents independently as defined above;

$$[L-H]^+[Z(A)_4]^- \text{ or } [L]^+[Z(A)_4]^-$$ [Chemical Formula 10]

wherein, in the formula, L is a neutral or cationic Lewis acid; H is a hydrogen atom; Z is a group 13 element; each A represents independently aryl having 6 to 20 carbon atoms or alkyl having 1 to 20 carbon atoms of which one or more hydrogen atoms are capable of being substituted with substituents; and the substituents are halogen, hydrocarbyl having 1 to 20 carbon atoms, alkoxy having 1 to 20 carbon atoms, or aryloxy having 6 to 20 carbon atoms.

7. The catalytic composition of claim 6, further comprising a reaction hydrocarbon solvent.

* * * * *